US007253155B2

(12) United States Patent
Keith et al.

(10) Patent No.: US 7,253,155 B2
(45) Date of Patent: Aug. 7, 2007

(54) COMBINATIONS FOR THE TREATMENT OF IMMUNOINFLAMMATORY DISORDERS

(75) Inventors: Curtis Keith, Boston, MA (US); Alexis Borisy, Boston, MA (US); Grant Zimmerman, Somerville, MA (US); Edward Roydon Jost-Price, West Roxbury, MA (US); Palaniyandi Manivasakam, Brighton, MA (US); Nicole Hurst, Boston, MA (US); Michael A. Foley, Chestnut Hill, MA (US)

(73) Assignee: CombinatoRx, Inc., Cambridge, MA (US)

( * ) Notice: Subject to any disclaimer, the term of this patent is extended or adjusted under 35 U.S.C. 154(b) by 0 days.

(21) Appl. No.: 10/264,991

(22) Filed: Oct. 4, 2002

(65) Prior Publication Data

US 2003/0119786 A1 Jun. 26, 2003

Related U.S. Application Data

(60) Provisional application No. 60/327,674, filed on Oct. 5, 2001.

(51) Int. Cl.
*A61K 31/56* (2006.01)
*A61K 31/517* (2006.01)

(52) U.S. Cl. ............... 514/171; 514/177; 514/179; 514/180; 514/258.1

(58) Field of Classification Search ............ 514/171, 514/177, 179, 180, 258.1
See application file for complete search history.

(56) References Cited

U.S. PATENT DOCUMENTS

| 3,934,036 | A | | 1/1976 | Irikura |
| 4,034,087 | A | | 7/1977 | Voorhees |
| 4,107,306 | A | | 8/1978 | Voorhees |
| 4,367,217 | A | | 1/1983 | Gruber et al. |
| 4,499,093 | A | * | 2/1985 | Galabov et al. ......... 514/262.1 |
| 4,554,271 | A | | 11/1985 | Braughler et al. |
| 4,685,911 | A | | 8/1987 | Konno et al. |
| 4,879,119 | A | | 11/1989 | Konno et al. |
| 5,242,921 | A | | 9/1993 | Milstone et al. |
| 5,270,047 | A | | 12/1993 | Kauffman et al. |
| 5,314,688 | A | | 5/1994 | Kauffman et al. |
| 5,326,764 | A | | 7/1994 | Milstone et al. |
| 5,428,040 | A | | 6/1995 | Magolda et al. |
| 5,468,729 | A | | 11/1995 | Chretien et al. |
| 5,639,759 | A | | 6/1997 | Magolda et al. |
| 5,668,116 | A | | 9/1997 | Cullis-Hill et al. |
| 5,756,553 | A | | 5/1998 | Iguchi et al. |
| 5,762,918 | A | | 6/1998 | Thorpe |
| 5,792,476 | A | * | 8/1998 | Hallgren ............... 424/465 |
| 5,874,437 | A | | 2/1999 | Garvey et al. |
| 5,874,441 | A | | 2/1999 | Magolda et al. |
| 5,958,926 | A | | 9/1999 | Garvey et al. |
| 6,010,716 | A | | 1/2000 | Saunal et al. |
| 6,015,577 | A | | 1/2000 | Eisert et al. |
| 6,054,487 | A | | 4/2000 | Sekut et al. |
| 6,071,514 | A | | 6/2000 | Grinnell et al. |
| 6,110,910 | A | | 8/2000 | Magolda et al. |
| 6,133,272 | A | | 10/2000 | Garvey et al. |
| 6,172,060 | B1 | | 1/2001 | Garvey et al. |
| 6,172,068 | B1 | | 1/2001 | Garvey et al. |
| 6,177,428 | B1 | | 1/2001 | Garvey et al. |
| 6,197,778 | B1 | | 3/2001 | Garvey et al. |
| 6,197,782 | B1 | | 3/2001 | Garvey et al. |
| 6,211,179 | B1 | | 4/2001 | Garvey et al. |
| 6,221,881 | B1 | | 4/2001 | Garvey et al. |
| 6,232,321 | B1 | | 5/2001 | Garvey et al. |
| 6,265,427 | B1 | | 7/2001 | Camden |
| 6,316,457 | B1 | | 11/2001 | Kapaan et al. |
| 6,331,543 | B1 | | 12/2001 | Garvey et al. |
| 6,337,325 | B1 | | 1/2002 | Schonharting et al. |
| 6,372,254 | B1 | | 4/2002 | Ting et al. |
| 6,383,471 | B1 | | 5/2002 | Chen et al. |
| 6,403,571 | B2 | | 6/2002 | Gould et al. |
| 6,462,044 | B2 | | 10/2002 | Garvey et al. |
| 6,602,521 | B1 | | 8/2003 | Ting et al. |
| 6,677,326 | B2 | | 1/2004 | Bardsley et al. |
| 6,730,321 | B2 | | 5/2004 | Ting et al. |
| 2001/0007083 | A1 | | 7/2001 | Roorda et al. |
| 2001/0016604 | A1 | | 8/2001 | Yu et al. |
| 2002/0019405 | A1 | | 2/2002 | Garvey et al. |
| 2003/0003151 | A1 | | 1/2003 | Chopra |
| 2003/0023087 | A1 | | 1/2003 | Garvey et al. |
| 2003/0069169 | A1 | | 4/2003 | Macor et al. |
| 2003/0077229 | A1 | | 4/2003 | Dugger, III |
| 2003/0203028 | A1 | | 10/2003 | Ting et al. |
| 2004/0087486 | A1 | | 5/2004 | Hanson |
| 2004/0087591 | A1 | | 5/2004 | Garvey et al. |
| 2004/0180812 | A1 | | 9/2004 | Dicker et al. |
| 2005/0025713 | A1 | | 2/2005 | Dugger, III |
| 2005/0058688 | A1 | | 3/2005 | Boerger et al. |

FOREIGN PATENT DOCUMENTS

CN 1246335 A 3/2000

(Continued)

OTHER PUBLICATIONS

Berkow et al "Merck Manual of Medical Information," Home edition, 1997, pp. 248-255.*

(Continued)

*Primary Examiner*—Shengjun Wang
(74) *Attorney, Agent, or Firm*—Clark & Elbing LLP

(57) ABSTRACT

The invention features a method for treating a patient having an immunoinflammatory disorder, by administering to the patient (i) a tetra-substituted pyrimidopyrimidine, and (ii) a corticosteroid simultaneously or within 14 days of each other in amounts sufficient to reduce or inhibit immunoinflammation.

54 Claims, No Drawings

FOREIGN PATENT DOCUMENTS

| | | | |
|---|---|---|---|
| EP | 0 303 713 B1 | | 8/1988 |
| EP | 0 543 653 A1 | | 11/1992 |
| EP | 1093814 | * | 4/2001 |
| GB | 2 292 079 A | | 2/1996 |
| WO | WO 92/16226 | | 1/1992 |
| WO | WO 92/16226 A | | 10/1992 |
| WO | WO 98/19672 | | 5/1998 |
| WO | WO 98/55142 | | 12/1998 |
| WO | WO 99/16417 | | 4/1999 |
| WO | WO 99/62537 | * | 12/1999 |
| WO | WO 00/12076 | | 3/2000 |
| WO | WO 00/12497 | | 3/2000 |
| WO | WO 00/59475 | | 10/2000 |
| WO | WO 01/47572 A2 | | 7/2001 |
| WO | WO 01/54679 A2 | | 8/2001 |
| WO | WO 01/68056 A1 | | 9/2001 |
| WO | WO 02/085304 A2 | | 10/2002 |
| WO | WO 02/094227 A1 | | 11/2002 |
| WO | WO 03/043603 A1 | | 5/2003 |
| WO | WO 2004/019909 A2 | | 3/2004 |
| WO | WO 2004/069254 A2 | | 8/2004 |
| WO | WO 2005/020933 A2 | | 3/2005 |

OTHER PUBLICATIONS

Berkow et al. The Merck Manual, fifteenth edition, 1987, pp. 797-807.*
Sadamoto et al. 'Thrombotic thrombocytopenic purpura in a patient with diffuse form of systemic sclerosis,' Japanese Journal of Rheumatology, 1999, vol. 9, No. 3, pp. 267-272.*
Barlow et al., "Resistance-modifying agents. Part 7: 2,6-disubstituted-4,8-dibenzylaminopyrimido[5,4-d]pyrimidines that inhibit nucleoside transport in the presence of $\alpha_1$-acid glycoprotein (AGP)" Bioorganic & Medicinal Chemistry Letters 10:585-589 (2000).
Cass et al., "A comparison of the abilities of nitrobenzylthioinosine, dilazep, and dipyridamole to protect human hematopoietic cells from 7-deazaadenosine (tubercidin)" Cancer Research 52:5879-5886 (1992).
Cazenave et al., "Inhibition of platelet adherence to a collagen-coated surface by nonsteroidal anti-inflammatory drugs, pyrimido-pyrimidine and tricyclic compounds, and lidocaine" J. Lab. Clin. Med. 83:797-806 (1974).
Curtin et al., "Potentiation of the cytotoxicity of thymidylate synthase (TS) inhibitors by dipyridamole analogues with reduced $\alpha_1$-acid glycoprotein binding" British Journal of Cancer 80:1738-1746 (1999).
Goh et al., "Nitrobenzylthioinosine-binding protein overexpression in human breast, liver, stomach and colorectal tumour tissues" Anticancer Research 15:2575-2580 (1995).
Harada et al., "Renal amyloidosis associated with crescentic glomerulonephritis" Am. J. Nephrol. 4:52-55 (1984).
Konstantinov et al., "Interferon response to dipyridamole in lupus erythematosus patients" British Journal of Dermatology 121:59-63 (1989).
Lau et al., "Reduced red blood cell deformability in patients with rheumatoid vasculitis. Improvement after in vitro treatment with dipyridamole" Arthritis & Rheumatism 38:248-253 (1995).
Lehman and Danenberg, "Modulation of RTX cytotoxicity by thymidine and dipyridamole in vitro: implications for chemotherapy" Cancer Chemother. Pharmacol. 45:142-148 (2000).
Maezawa et al., "Combined treatment with cyclophosphamide and prednisolone can induce remission of nephrotic syndrome in a patient with renal amyloidosis, associated with rheumatoid arthritis" Clinical Nephrology 42:30-32 (1994).
Vraux et al., "Inhibition of human monocyte TNF production by adenosine receptor agonsits" Life Sciences 52:1917-1924 (1993).
Ziemnicka-Merchant et al., "Effects of chemical modification of nitrobenzyl thioinosine on its binding to high-affinity membrane binding sites and inhibition of nucleoside transport" Biochemical Pharmacology 44:1577-1583 (1992).
Brunette et al., "Long-term Immunosuppressive Treatment of a Child with Takayasu's Arteritis and High IgE Immunoglobulins," Pediatr. Nephrol. 10:67-69 (1996).
Bruserud, "Dipyridamol Inhibits Activation of Human T Lymphocytes In Vitro," Clin. Immunol. Immunopathol. 42:102-109 (1987).
Eigler et al., "Endogenous Adenosine Curtails Lipopolysaccharide-Stimulated Tumour Necrosis Factor Synthesis," Scan J. Immunol. 45:132-139 (1997).
Haskó et al., "Adenosine Inhibits IL-12 and TNF-α Production Via Adenosine $A_{2a}$ Receptor-Dependent and Independent Mechanisms," FASEB J. 14:2065-2074 (2000).
Iijima et al., "Multiple Combined Therapy for Severe Henoch-Schönlein Nephritis in Children," Pediatr. Nephrol. 12:244-248 (1998).
Nenci et al., "Effects of Dipyridamole on the Hypoxemic Pulmonary Hypertension of Patients with Chronic Obstructive Pulmonary Disease," Respiration 53:13-19 (1988).
Rossi et al., "Thrombotic Thrombocytopenic Purpura," JAMA 228:1141-1143 (1974).
Takeda et al., "Long-Term Corticosteroid and Dipyridamole Treatment of Membranoproliferative Glomerulonephritis Type I in Children," Jpn J Nephrol 37:330-335 (1995).
Wagner et al., "Adenosine Inhibits Lipopolysaccharide-Induced Cardiac Expression of Tumor Necrosis Factor-α," Circ. Res. 82:47-56 (1998).
Yoshikawa et al., "Combined Therapy with Prednisolone, Azathioprine, Heparin-Warfarin, and Dipyridamole for Paediatric Patients with Severe IgA Nephropathy-Is it Relevant for Adult Patients?" Nephrol Dial Transplant 14:1097-1099 (1999).
Afeltra, "Treatment of Rheumatoid Arthritis: New Therapeutic Approaches with Biological Agents," Curr. Drug Targets Immune Endocr. Metabol. Disord. 1:45-65 (2001).
Badger et al., "Disease-Modifying Activity of SB 242235, A Selective Inhibitor of p38 Mitogen-Activated Protein Kinase, In Rat Adjuvant-Induced Arthritis," Arthritis Rheum. 43:175-183 (2000).
Barnes, "Anti-inflammatory Actions of Glucocorticoids: Molecular Mechanisms," Clin. Sci. 94:557-572 (1998).
Baxter et al., "Mechanism of Glucocorticoid Action: General Features with Reference to Steroid-Mediated Immunosuppression," Transplant. Proc. 7:55-65 (1975).
Berger et al., "Comparative Carcinogenic Activity of Prednimustine, Chlorambucil, Prednisolone and Chlorambucil Plus Prednisolone in Sprague-Dawley Rats," Arch. Geschwulstforsch55:429-442 (1985).
Berger et al., "Long-Term Toxicology Effects of Prednimustine in Comparison with Chlorambucil, Prednisolone, and Chlorambucil Plus Prednisolone in Sprague-Dawley Rats," Semin. Oncol. 13:8-13 (1986).
Conway et al., "Inhibition of Cartilage and Bone Destruction in Adjuvant Arthritis in the Rat by a Matrix Metalloproteinase Inhibitor," J. Exp. Med. 182:449-457 (1995).
Feldmann et al., "Anti-TNFα Therapy of Rheumatoid Arthritis: What Have We Learned?," Annu. Rev. Immunol. 19:163-196 (2001).
Mancini et al., "Inhibition of Tumor Necrosis Factor-α (TNF-α)/TNF- α Receptor Binding by Structural Analogues of Suramin," Biochem. Pharmacol. 58:851-859 (1999).
Ryrfeldt et al., "Liver Tumors in Male Rats Following Treatment with Glucocorticosteroids," Toxicol. Pathol. 20:115-117 (1992).
Ardizzone et al., "Inflammatory Bowel Disease: New Insights Into Pathogenesis and Treatment," J. Intern. Med. 252:475-496 (2002).
Badger et al., "Disease-Modifying Activity of SB 242235, A Selective Inhibitor of p38 Mitogen-Activated Protein Kinase, in Rat Adjuvant-Induced Arthiritis," Arth. Rheum. 43:175-183 (2000).
Beck et al., "Increased Production of Interferon Gamma and Tumor Necrosis Factor Precedes Clinical Manifestation in Multiple Sclerosis: Do Cytokines Trigger Off Exacerbations?" Acta. Neurol. Scand. 78:318-323 (1998).
Braun et al. "Anti-tumour Necrosis Factor α Therapy for Ankylosing Spondylitis: International Experience," Ann. Rheum. Dis. 61:iii51-iii60 (2002).

Braun et al., "Therapy of Ankylosing Spondylitis and Other Spondyloarthritides: Established Medical Treatment, Anti-TNF-α Therapy and Other Novel Approaches," *Arthritis. Res.* 4:307-321 (2002).

Crew et al., "Transgenic Mice Expressing a Truncated *Peromyscus Leucopus* TNF-α Gene Manifest an Arthritis Resembling Ankylosing Spondylitis," *J. Interferon Cytokine Res.* 18:219-225 (1998).

Durie et al., "Collagen-Induced Arthritis as a Model of Rheumatoid Arthritis," *Clin. Immunol. Immunopathol.* 73:11-18 (1994).

Edwards et al., "PEGylated Recombinant Human Soluble Tumour Necrosis Factor Receptor Type 1 (r-Hu-sTNF-R1): Novel High Affinity TNF Receptor Designed For Chronic Inflammatory Diseases," *Ann. Rheum. Dis.* 58:173-181 (1999).

Ettehadi et al., "Elevated Tumour Necrosis Factor-Alpha (TNF-α) Biological Activity in Psoriatic Skin Lesions," *Clin. Exp. Immunol.* 96:146-151 (1994).

Ganesan et al., "Therapeutic Inhibitors of Tumor Necrosis Factor in Crohn's Disease," *Curr. Op. Invest. Drugs* 3:1301-1306 (2002).

Gorman et al., "Treatment of Ankylosing Spondylitis by Inhibition of Tumor Necrosis Factor α," *N. Eng. J. Med.* 346:1349-1356 (2002).

Khoury et al., "Changes in Serum Levels of ICAM and TNF-R Correlate With Disease Activity in Multiple Sclerosis," *Neurology* 53:758 (1999).

Krueger et al., "Potential of Tumor Necrosis Factor Inhibitors in Psoriasis and Psoriatic Arthritis," *Arch. Dermator.* 140:218-225 (2004).

Lichtenstein et al., "Is Infliximab Effective for Induction of Remission in Patients With Ulcerative Colitis?" *Inflammatory Bowel Diseases* 7:89-93 (2001).

Moreland et al., "Etanercept Therapy in Rheumatoid Arthritis," *Ann. Intern. Med.* 130:478-486 (1999).

Mpofu et al., "Anti-TNF-α Therapies: They Are All the Same (Aren't They?)," *Rheumatology* 44:271-272 (2005).

Murch et al., "Location of Tumour Necrosis Factor α by Immunohistochemistry in Chronic Inflammatory Bowel Disease," *Gut* 34:1705-1709 (1993).

Nanda et al., "Etanercept: a Clinical Review of Current and Emerging Indications," *Expert. Opin. Pharmacother.* 5:1175-1186 (2004).

Nikolaus et al., "Mechanisms in Failure of Infliximab for Crohn's Disease," *Lancet* 356:1475-1479 (2000).

Raza et al., "Anti-TNF Therapies in Rheumatoid Arthritis, Crohn's Disease, Sepsis, and Myelodysplastic Syndromes," *Microsc. Res. Techn.* 50:229-235 (2000).

Sandborn et al., "Etanercept for Active Crohn's Disease: A Randomized, Double-Blind, Placebo-Controlled Trial," *Gastroenterology* 121:1088-1094 (2001).

Sands et al., "Biological Therapies for Ulcerative Colitis," *Acta. Gastro-Enterologica Belgica* 64:205-209 (2001).

Schreiber et al., "Tumour Necrosis Factor α and Interleukin 1β in Relapse of Crohn's Disease," *Lancet* 353:459-461 (1999).

Selmaj et al., "Identification of Lymphotoxin and Tumor Necrosis Factor in Multiple Sclerosis Lesions," *J. Clin. Invest.* 87:949-954 (1991).

Sharief et al., "Association Between Tumor Necrosis Factor-α and Disease Progression in Patients with Multiple Sclerosis," *N. Eng. J. Med.* 325:467-472 (1991).

Shen et al., "Current Therapeutic Recommendations, *Infliximab for Ulcerative Colitis*," *J. Clin. Gastroenterol.* 38:741-745 (2004).

Shou et al., "Identification of Blood Biomarkers of Rheumatoid Arthritis by Transcript Profiling of Peripheral Blood Mononuclear Cells From the Rat Collagen-Induced Arthritis Model," *Arthritis Res. Ther.* 8:R28 (2006).

Sieper et al., "New Treatment Options in Ankylosing Spondylitis: a Role for Anti-TNFα Therapy," *Ann. Rheum. Dis.* 60:iii58-iii61 (2001).

Vladic et al., "Cerebrospinal Fluid and Serum Protein Levels of Tumour Necrosis Factor-Alpha (TNF-α), Interleukin-6 (IL-6) and Soluble Interleukin-6 Receptor (sIL-6Rgp80) in Multiple Sclerosis Patients," *Cytokine* 20:86-89 (2002).

\* cited by examiner

COMBINATIONS FOR THE TREATMENT OF IMMUNOINFLAMMATORY DISORDERS

CROSS-REFERENCE TO RELATED APPLICATIONS

This application claims benefit of the filing date of the copending U.S. Provisional Application No. 60/327,674 (filed Oct. 5, 2001), hereby incorporated by reference.

FIELD OF THE INVENTION

The invention relates to the treatment of immunoinflammatory disorders.

BACKGROUND OF THE INVENTION

Immunoinflammatory disorders (e.g., rheumatoid arthritis, psoriasis, ulcerative colitis, Crohn's disease, stroke-induced brain cell death, ankylosing spondylitis, fibromyalgia, and inflammatory dermatoses, asthma, multiple sclerosis, type I diabetes, systemic lupus erythematosus, scleroderma, systemic sclerosis, and Sjögren's syndrome) are characterized by dysregulation of the immune system and inappropriate activation of the body's defenses, resulting in damage to healthy tissue.

One percent of humans world-wide are afflicted with rheumatoid arthritis (RA), a relentless, progressive disease causing severe swelling, pain, and eventual deformity and destruction of joints. According to the Arthritis Foundation, rheumatoid arthritis currently affects over two million Americans, of which women are three times more likely to be afflicted. Rheumatoid arthritis is characterized by inflammation of the lining of the joints and/or other internal organs, and the presence of elevated numbers of lymphocytes and high levels of proinflammatory cytokines.

Diagnosis of RA generally includes: (i) morning stiffness in joints lasting at least one hour before improvement, (ii) arthritis of three or more joint areas having simultaneously soft tissue swelling or fluid; (iii) arthritis of at least one hand joint; (iv) symmetric arthritis, i.e., simultaneous involvement of the same joint area on both sides of the body; (v) rheumatoid nodules; (vi) abnormal serum rheumatoid factor; and (vii) radiographic changes typical of rheumatoid arthritis on posteroanterior hand and wrist radiographs, which include erosions or unequivocal bony decalcification localized in or most marked adjacent to the involved joints. Patients are classified as having RA if at least four of these seven criteria, and (i) through (iv) must have been present for at least six weeks. (American College of Rheumatology, 1987 Criteria for the Classification of Acute Arthritis of Rheumatoid Arthritis, based on Arnett F C et al., Arthritis Rheum. 1988; 31:315-324). Pain per se is not required for the diagnosis of RA.

Treatment of RA generally includes anti-inflammatory strategies directed at suppressing the clinical manifestations of joint inflammation, including synovial thickening, joint tenderness, and joint stiffness. Drugs used to address these signs and symptoms generally include (i) non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate)—these drugs may be adequate for mild RA, but do not appear to alter the longterm course of the disease; and (ii) steroids (e.g., cortisone, dexamethasone, hydrocortisone, methylprednisolone, prednisolone, prednisone, triamcinolone).

Treatment for RA may also include strategies directed at limiting the long term joint damage and deformity caused by the inflammation in the joints. Such treatments are generally described as DMARDs, i.e., disease modifying antirheumatic drugs (e.g., cyclosporine, azathioprine, methotrexate, leflunomide, cyclophosphamide, hydroxychloroquine, sulfasalazine, D-penicillamine, minocycline, gold, etanercept (soluble TNF receptor) and infliximab (a chimeric monoclonal anti-THF antibody)).

There is a need to develop new regimens for the treatment of immunoinflammatory disorders.

SUMMARY OF THE INVENTION

We have discovered that the combination of tetra-substituted pyrimidopyrimidines, such as dipyridamole (also known as 2,6-bis(diethanolamino)-4,8-dipiperidinopyrimido(5,4-d)pyrimidine), and corticosteroids, such as fludrocortisone (as known as 9-alpha-fluoro-11-beta, 17-alpha, 21-trihydroxy-4-pregnene-3,20-dione acetate), and prednisolone (also known as 1-dehydrocortisol; 1-dehydrohydrocortisone; or 1,4-pregnadiene-11beta, 17alpha,21-triol-3,20-dione; or 11beta,17alpha,21-trihydroxy-1,4-pregnadiene-3,20-dione), brings about substantial suppression of TNFα levels induced in peripheral blood mononuclear cells (PBMCs).

Accordingly, the invention features, in one aspect, a method for treating a patient who has, or who is at risk for developing, an immunoinflammatory disorder. The method includes administering (i) a corticosteroid; and (ii) a tetra-substituted pyrimidopyrimidine having the formula (I):

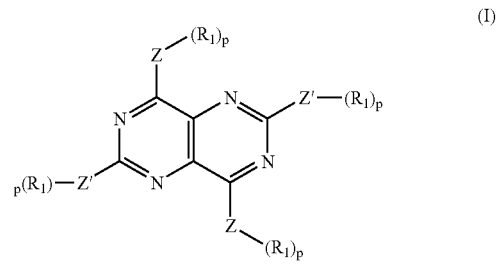

wherein each Z and each Z' is, independently, N, O, C,

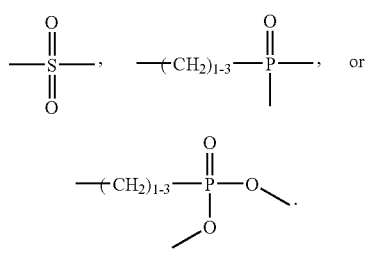

When Z or Z' is O or

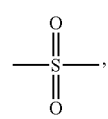

then p=1, when Z or Z' is N,

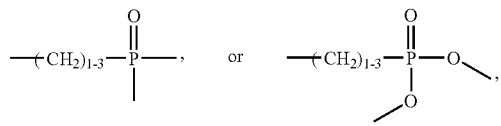

then p=2, and when Z or Z' is C, then p=3. In formula (I), each $R_1$ is, independently, X, OH, N-alkyl (wherein the alkyl group has 1 to 20, more preferably 1-5, carbon atoms); a branched or unbranched alkyl group having 1 to 20, more preferably 1-5, carbon atoms; or a heterocycle, preferably as defined in formula (Y), below. Alternatively, when p>1, two $R_1$ groups from a common Z or Z' atom, in combination with each other, may represent —$(CY_2)_k$— in which k is an integer between 4 and 6, inclusive. Each X is, independently, Y, $CY_3$, $C(CY_3)_3$, $CY_2CY_3$, $(CY_2)_{1-5}OY$, substituted or unsubstituted cycloalkane of the structure $C_nY_{2n-1}$, wherein n=3-7, inclusive. Each Y is, independently, H, F, Cl, Br, or I. In one embodiment, each Z is the same moiety, each Z' is the same moiety, and Z and Z' are different moieties. The two compounds are each administered in an amount that, when combined with the second compound, is sufficient to treat or prevent the immunoinflammatory disorder.

In a related aspect, the invention features a method for suppressing the production of one or more proinflammatory cytokines in a patient in need thereof by administering to the patient (i) a corticosteroid; and (ii) a tetra-substituted pyrimidopyrimidine having formula (I).

In particularly useful tetra-substituted pyrimidopyrimidines in both aspects of the invention, $R_1$ is a substituted or unsubstituted furan, purine, or pyrimidine, $(CH_2CH_2OY)$, $(CH_2CH(OH)CH_2OY)$, $(HCH_2CH(OH)CX_3)$, $((CH_2)_nOY)$, where n=2-5,

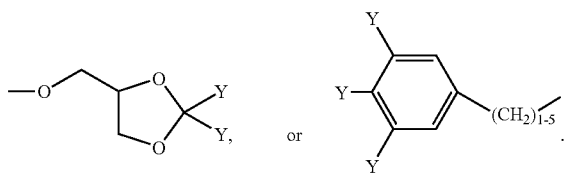

In other useful tetra-substituted pyrimidopyrimidines, each Z is N and the two associated $R_1$ groups combine in the form of —$(CH_2)_5$—, and each Z' is N and each Z'-associated $R_1$ group is —$CH_2CH_2OH$.

The tetra-substituted pyrimidopyrimidine and the corticosteroid may be present in pharmaceutical compositions that contain a pharmaceutically acceptable carrier, diluent, or excipient, and are administered at dosages and frequencies sufficient to suppress TNFα levels enough to produce a therapeutic benefit to the patient. The tetra-substituted pyrimidopyrimidine and the corticosteroid can be administered within 14 days of each other (e.g., within 10 days, within five days, twenty-four hours, or one hour of each other, or even simultaneously). Administration of each compound can occur, e.g., 1 to 5 times each day, or as necessary to alleviate symptoms.

Accordingly, this invention also features pharmaceutical compositions, pharmaceutical packs, and kits containing one or more tetra-substituted pyrimidopyrimidine and one or more corticosteroid. The methods and compositions (pharmaceutical compositions and pharmaceutical packs) of the invention may feature higher order combinations of tetra-substituted pyrimidopyrimidines and corticosteroids. Specifically, one, two, three, or more tetra-substituted pyrimidopyrimidines may be combined with one, two, three, or more corticosteroids. In preferred embodiments, the tetra-substituted pyrimidopyrimidine, the corticosteroid, or both are approved by the United States Food and Drug Administration (USFDA) for administration to a human.

Exemplary tetra-substituted pyrimidopyrimidines that are useful in the methods and compositions of this invention include 2,6-disubstituted 4,8-dibenzylaminopyrimido[5,4-d] pyrimidines. Particularly useful tetra-substituted pyrimidopyrimidines include dipyridamole (also known as 2,6-bis (diethanolamino)-4,8-dipiperidinopyrimido(5,4-d) pyrimidine), mopidamole, dipyridamole monoacetate, NU3026 (2,6-di-(2,2-dimethyl-1,3-dioxolan-4-yl)-methoxy-4,8-di-piperidinopyrimidopyrimidine), NU3059 (2,6-bis-(2,3-dimethyoxypropoxy)-4,8-di-piperidinopyrimidopyrimidine), NU3060 (2,6-bis[N,N-di(2-methoxy)ethyl]-4,6-di-piperidinopyrimidopyrimidine), and NU3076 (2,6-bis (diethanolamino)-4,8-di-4-methoxybenzylaminopyrimidopyrimidine).

The invention described herein has been exemplified using the corticosteroids fludrocortisone; however, a skilled artisan will recognize that structural and functional analogs of these corticosteroids can also be used in combination with the tetra-substituted pyrimidopyrimidines in the methods and compositions of the present invention. Other useful corticosteroids may be identified based on the shared structural features and mechanism of action among the corticosteroid family.

The tetra-substituted pyrimidopyrimidine and the corticosteroid may be administered in the same or different pharmaceutical formulations. Pharmaceutical compositions or components of the pharmaceutical pack may be administered by the same or different routes and include oral, rectal, intravenous, intramuscular, subcutaneous, intra-articular, inhalation, topical or transdermal, vaginal, and ophthalmic administration.

Dosages of the tetra-substituted pyrimidopyrimidine and the corticosteroid may be determined individually. In prior art therapeutic regimines, tetra-substituted pyrimidopyrimidine are typically administered to human patients at about 0.5-800 mg/day, 18-600 mg/day, or 50-400 mg/day. Corticosteroids are typically administered at about 0.1-1500 mg/day, 0.5-30 mg/day, or 0.5-10 mg/day. Low doses of corticosteroids (e.g., 10 mg/day or less of prednisolone, or its equivalent) are preferred. In the methods and compositions of the invention, both components typically will be used in lower dosages than those given above, because the two drugs operate together to treat or suppress the subject disorder. Thus, the pyrimidopyrimidine can be used, according to the invention, at a dosage of 0.5-50 mg/day, and the corticosteroid can be used at a dosage of 0.1 to 10 mg/day. The total daily dosage of the tetra-substituted pyrimidopyrimidine and the corticosteroid may be administered in one, two, three, four, or more dosages. It is not necessary for the tetra-substituted pyrimidopyrimidine and the corticosteroid to be administered in the same number of daily doses. Further, there is no need for the tetra-substituted pyrimidopyrimidine and/or the corticosteroid to be administered every day or by the same route of administration. For example, the tetra-substituted pyrimidopyrimidine may be administered by intravenous injection every second day and the corticosteroid administered by topical application twice every day. Accordingly, when administered in different compositions, pharmaceutical formulations, packs, and kits are prepared in form and dosage suitable for achieving the desired treatment regimen.

The diseases or disorders treated using the methods and compositions of this invention are immunoinflammatory disorders including, for example, rheumatoid arthritis, psoriasis, ulcerative colitis, Crohn's disease, stroke-induced brain cell death, ankylosing spondylitis, fibromyalgia, asthma, multiple sclerosis, type I diabetes, systemic lupus erythematosus, scleroderma, systemic sclerosis, inflammatory dermatoses, or Sjögren's syndrome.

The invention also features a method for identifying compounds useful for treating a patient having an immunoinflammatory disorder. The method includes the steps of: contacting immune cells in vitro with (i) an immunomodulatory compound selected from the group of a tetra-substituted pyrimidopyrimidine having formula (I) or a corticosteroid; and (ii) a candidate compound, and determining whether the immune response is modulated relative to (a) immune cells contacted with the immunomodulatory compound but not contacted with the candidate compound, and (b) immune cells contacted with the candidate compound but not with the immunomodulatory compound. A candidate compound that, when combined with an immunomodulatory compound, modulates the immune response to a greater degree than controls, is a compound that is potentially useful for treating a patient having an immunoinflammatory disorder.

Compounds useful in the invention include those described herein in any of their pharmaceutically acceptable forms, including isomers such as diastereomers and enantiomers, salts, solvates, and polymorphs thereof, as well as racemic mixtures of the compounds described herein.

By "heterocycle" is meant any cyclic molecule, wherein one or more of the ring atoms is an atom other than carbon. Preferable heterocycles consist of one or two ring structures. Preferable heteroatoms are N, O, and S. Each ring structure of the heterocycle consists of 3-10 atoms, preferably 4-8 atoms, and most preferably 5-7 atoms. Each ring structure need not contain a heteroatom, provided that a heteroatom is present in at least one ring structure. Preferred heterocycles are, for example, beta-lactams, furans, tetrahydrofurans, pyrroles, pyrrolidines, thiophenes, tetrahydrothiophenes, oxazoles, imidazolidine, indole, guanine, and phenothiazine.

By "patient" is meant any animal (e.g., a human).

The term "immunoinflammatory disorder" encompasses a variety of conditions, including autoimmune diseases. Immunoinflammatory disorders result in the destruction of healthy tissue by an inflammatory process. Examples of immunoinflammatory disorders include, rheumatoid arthritis, psoriasis, ulcerative colitis, Crohn's disease, stroke-induced brain cell death, ankylosing spondylitis, fibromyalgia, asthma, multiple sclerosis, type I diabetes, systemic lupus erythematosus, scleroderma, systemic sclerosis, inflammatory dermatoses, myasthenia gravis, and Sjögren's syndrome.

By "corticosteroid" is meant any naturally occurring or synthetic steroid hormone which can be derived from cholesterol and is characterized by a hydrogenated cyclopentanoperhydrophenanthrene ring system. Naturally occurring corticosteroids are generally produced by the adrenal cortex. Synthetic corticosteroids may be halogenated. Functional groups required for activity include a double bond at $\Delta 4$, a C3 ketone, and a C20 ketone. Corticosteroids may have glucocorticoid and/or mineralocorticoid activity. In preferred embodiments, the corticosteroid is either fludrocortisone or prednisolone.

Exemplary corticosteroids include algestone, 6-alpha-fluoroprednisolone, 6-alpha-methylprednisolone, 6-alpha-methylprednisolone 21-acetate, 6-alpha-methylprednisolone 21-hemisuccinate sodium salt, 6-alpha,9-alpha-difluoroprednisolone 21-acetate 17-butyrate, amcinafal, beclomethasone, beclomethasone dipropionate, beclomethasone dipropionate monohydrate, 6-beta-hydroxycortisol, betamethasone, betamethasone-17-valerate, budesonide, clobetasol, clobetasol propionate, clobetasone, clocortolone, clocortolone pivalate, cortisone, cortisone acetate, cortodoxone, deflazacort, 21-deoxycortisol, deprodone, descinolone, desonide, desoximethasone, dexamethasone, dexamethasone-21-acetate, dichlorisone, diflorasone, diflorasone diacetate, diflucortolone, doxibetasol, fludrocortisone, flumethasone, flumethasone pivalate, flumoxonide, flunisolide, fluocinonide, fluocinolone acetonide, 9-fluorocortisone, fluorohydroxyandrostenedione, fluorometholone, fluorometholone acetate, fluoxymesterone, flupredidene, fluprednisolone, flurandrenolide, formocortal, halcinonide, halometasone, halopredone, hyrcanoside, hydrocortisone, hydrocortisone acetate, hydrocortisone butyrate, hydrocortisone cypionate, hydrocortisone sodium phosphate, hydrocortisone sodium succinate, hydrocortisone probutate, hydrocortisone valerate, 6-hydroxydexamethasone, isoflupredone, isoflupredone acetate, isoprednidene, meclorisone, methylprednisolone, methylprednisolone acetate, methylprednisolone sodium succinate, paramethasone, paramethasone acetate, prednisolone, prednisolone acetate, prednisolone metasulphobenzoate, prednisolone sodium phosphate, prednisolone tebutate, prednisolone-21-hemisuccinate free acid, prednisolone-21-acetate, prednisolone-21(beta-D-glucuronide), prednisone, prednylidene, procinonide, tralonide, triamcinolone, triamcinolone acetonide, triamcinolone acetonide 21-palmitate, triamcinolone diacetate, triamcinolone hexacetonide, and wortmannin. Desirably, the corticosteroid is fludrocortisone or prednisolone.

By "an effective amount" is meant the amount of a compound, in a combination of the invention, required to treat or prevent an immunoinflammatory disease. The effective amount of active compound(s) used to practice the present invention for therapeutic treatment of conditions caused by or contributing to an inflammatory disease varies depending upon the manner of administration, the age, body weight, and general health of the patient. Ultimately, the attending physician or veterinarian will decide the appropriate amount and dosage regimen. Such amount is referred to as an effective amount.

By the term "cytokine suppressing amount" is meant an amount of the combination which will cause a decrease in the vivo presence or level of the proinflammatory cytokine, when given to a patient for the prophylaxis or therapeutic treatment of an immunoinflammatory disorder which is exacerbated or caused by excessive or unregulated proinflammatory cytokine production.

Other features and advantages of the invention will be apparent from the following detailed description, and from the claims.

DETAILED DESCRIPTION

We have discovered that the combination of a tetra-substituted pyrimidopyrimidine with a corticosteroid substantially has substantial TNFα suppressing activity against stimulated white blood cells. The combinations of dipyridamole with fludrocortisone, and dipyridamole with prednisolone were particularly effective. Thus, the combination of a tetra-substituted pyrimidopyrimidine with a corticosteroid is useful for the treatment of immunoinflammatory disorders.

Dipyridamole

Dipyridamole (2,6-bis(diethanolamino)-4,8-dipiperidinopyrimido(5,4-d)pyrimidine) is a tetra-substituted pyrimidopyrimidine that is used as a platelet inhibitor, e.g., to prevent blood clot formation following heart valve surgery and to reduced the moribundity associated with clotting disorders, including myocardial and cerebral infarction. Typically, anticoagulation therapy (prophylaxis or treatment) is effected by administering dipyridamole at about 75-200 mg b.i.d, t.i.d., or q.i.d. either alone or in combination with aspirin. In the invention, lower doses generally can be used, e.g., 20-80 mg, administered by any of the prior art routes.

Tetra-substituted Pyrimidopyrimidines

Tetra-substituted pyrimidopyrimidines are structural analogs that can replace dipyridamole in the methods and compositions of this invention. Tetra-substituted pyrimidopyrimidines generally are of formula (I), above.

Therapy

Combination therapy according to the invention may be performed alone or in conjunction with another therapy and may be provided at home, the doctor's office, a clinic, a hospital's outpatient department, or a hospital. Treatment generally begins at a hospital so that the doctor can observe the therapy's effects closely and make any adjustments that are needed. The duration of the combination therapy depends on the type of immunoinflammatory disorder being treated, the age and condition of the patient, the stage and type of the patient's disease, and how the patient responds to the treatment. Additionally, a person having a greater risk of developing an immunoinflammatory disorder (e.g., a person who is genetically predisposed or previously had an immunoinflammatory disorder) may receive prophylactic treatment to inhibit or delay an inflammatory response.

The dosage, frequency and mode of administration of each component of the combination can be controlled independently. For example, one compound may be administered orally three times per day, while the second compound may be administered intramuscularly once per day. Combination therapy may be given in on-and-off cycles that include rest periods so that the patient's body has a chance to recovery from any as yet unforeseen side-effects. The compounds may also be formulated together such that one administration delivers both compounds.

Formulation of Pharmaceutical Compositions

The administration of each compound of the combination may be by any suitable means that results in a concentration of the compound that, combined with the other component, is antiinflammatory upon reaching the target region. The compound may be contained in any appropriate amount in any suitable carrier substance, and is generally present in an amount of 1-95% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance (sawtooth kinetic pattern); (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of compounds in the form of a controlled release formulation is especially preferred in cases in which the compound, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology, supra.

The two drugs may be mixed together in the tablet, or may be partitioned. In one example, the first drug is contained on the inside of the tablet, and the second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols and polvoxyethylene sorbitan fatty acid esters. Various additives, enhancers, or surfactants may be incorporated.

Compositions for Inhalation

For administration by inhalation, typical dosage forms include nasal sprays and aerosols. In a typically nasal formulation, the active ingredient(s) are dissolved or dispersed in a suitable vehicle. The pharmaceutically acceptable vehicles and excipients (as well as other pharmaceutically acceptable materials present in the composition such as diluents, enhancers, flavoring agents, and preservatives) are selected in accordance with conventional pharmaceutical practice in a manner understood by the persons skilled in the art of formulating pharmaceuticals.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE™. Examples of chelating agents are sodium EDTA, citric acid, and phosphoric acid. Examples of gel forming agents are CARBOPOL™, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN™)).

The pharmaceutical compositions described above for topical administration on the skin may also be used in connection with topical administration onto or close to the part of the body that is to be treated. The compositions may be adapted for direct application or for introduction into relevant orifice(s) of the body (e.g., rectal, urethral, vaginal or oral orifices). The composition may be applied by means of special drug delivery devices such as dressings or alternatively plasters, pads, sponges, strips, or other forms of suitable flexible material.

Controlled Release Percutaneous and Topical Compositions

There are several approaches for providing rate control over the release and transdermal permeation of a drug, including: membrane-moderated systems, adhesive diffusion-controlled systems, matrix dispersion-type systems, and microreservoir systems. A controlled release percutaneous and/or topical composition may be obtained by using a suitable mixture of the above-mentioned approaches.

In a membrane-moderated system, the active drug is present in a reservoir which is totally encapsulated in a shallow compartment molded from a drug-impermeable laminate, such as a metallic plastic laminate, and a rate-controlling polymeric membrane such as a microporous or a non-porous polymeric membrane (e.g., ethylene-vinyl acetate copolymer). The active compound is only released through the rate-controlling polymeric membrane. In the drug reservoir, the active drug substance may either be dispersed in a solid polymer matrix or suspended in a viscous liquid medium such as silicone fluid. On the external surface of the polymeric membrane, a thin layer of an adhesive polymer is applied to achieve an intimate contact of the transdermal system with the skin surface. The adhesive polymer is preferably a hypoallergenic polymer that is compatible with the active drug.

In an adhesive diffusion-controlled system, a reservoir of the active drug is formed by directly dispersing the active drug in an adhesive polymer and then spreading the adhesive containing the active drug onto a flat sheet of substantially drug-impermeable metallic plastic backing to form a thin drug reservoir layer. A matrix dispersion-type system is characterized in that a reservoir of the active drug substance is formed by substantially homogeneously dispersing the active drug substance in a hydrophilic or lipophilic polymer matrix and then molding the drug-containing polymer into a disc with a substantially well-defined surface area and thickness. The adhesive polymer is spread along the circumference to form a strip of adhesive around the disc.

In a microreservoir system, the reservoir of the active substance is formed by first suspending the drug solids in an aqueous solution of water-soluble polymer, and then dispersing the drug suspension in a lipophilic polymer to form a plurality of microscopic spheres of drug reservoirs.

Dosages

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

As described above, the compound in question may be administered orally in the form of tablets, capsules, elixirs or syrups, or rectally in the form of suppositories. Parenteral administration of a compound is suitably performed, for example, in the form of saline solutions or with the compound incorporated into liposomes. In cases where the compound in itself is not sufficiently soluble to be dissolved, a solubilizer such as ethanol can be applied. Below, for illustrative purposes, the dosages for dipyridamole and fludrocortisone are described.

Routes of Administration

For oral, intramuscular, subcutaneous, topical, inhalation, rectal, vaginal and ophthalmic administration of the tetra-substituted pyrimidopyrimidine, the dosage used according to the invention is about 0.5-800 mg/day, preferably about 5-600 mg/day, 10-100 mg/day, and more preferably 0.5-50 mg/day. Administration can be one to four times daily for one day to one year, and may even be for the life of the patient. Chronic, long-term administration will be indicated in many cases. In some cases of serious illness, up to 1600 mg/day may be necessary. For intravenous administration of the tetra-substituted pyrimidopyrimidine, the dosage used is about 0.1-200 mg/day, preferably about 0.5-150 mg/day, 1-100 mg/day, and more preferably about 0.5-50 mg/day. Administration can be one to four times daily. Systemic dosing will result in steady-state plasma concentrations preferably of 0.1-7.0 µM, more preferably, 0.5-5.0 µM, and most preferably, 1.0-2.0 µM.

The dosage of the corticosteroid for use in combination with the tetra-substituted pyrimidopyrimidine is about 0.1-1500 mg/day, preferably about 0.5-30 mg/day, and more preferably about 0.1-10 mg/day. Administration can be one to four times daily for one day to one year, and may even be for the life of the patient. Chronic, long-term administration will be indicated in many cases. In cases of serious illness, dosages up to 3000 mg/day may be necessary.

The following examples are to illustrate the invention. They are not meant to limit the invention in any way.

EXAMPLE 1

Preparation of Pairwise Compound Mixed Combination Serial Dilution Matrix

Stock solutions at 16 mg/ml of dipyridamole, and 1.6 mg/ml of fludrocortisone acetate (Sigma-Aldrich, St. Louis, Mo.; catalog numbers D9766 and F6127, respectively) were made in dimethylsulfoxide (DMSO). The dipyridamole master plates were made by adding 25 µl of the concentrated stock solution to columns 3, 9, and 15 (rows C through N) of a polypropylene 384-well storage plate that had been pre-filled with 75 µl of anhydrous DMSO. Using a TomTec Quadra Plus liquid handler, the 25 µl of dipyridamole stock solution was serially diluted four times into the adjacent columns (columns 4-7, 10-13, 16-19). The sixth column (8, 14, and 20) did not receive any compound and served as a vehicle control. The fludrocortisone master plates were made by adding 25 µl of the concentrated stock solution to the appropriate wells (row C, columns 3-8; row C, columns 9-14; row C, columns 15-20; row I, columns 3-8; row I, columns 9-14; row I, columns 15-20) of the appropriate master polypropylene 384-well storage plate. These master plates had been pre-filled with 75 µl of anhydrous DMSO. Using the TomTec Quadra Plus liquid handler, the 25 µl was serially diluted four times in the adjacent rows (rows D-G, and J-M). The sixth row (H and N) did not receive any compound to serve as a vehicle control. Master plates were sealed and stored at −20 C. until ready for use.

The final dipyridamole/fludrocortisone combination plates were generated by transferring 1 µl from each of the dipyridamole and fludrocortisone master plates to a dilution plate containing 100 µl of media (RPMI; Gibco BRL, #11875-085), 10% Fetal Bovine Serum (Gibco BRL, #25140-097), 2% Penicillin/Streptomycin (Gibco BRL, #15140-122)) using the TomTec Quadra Plus liquid handler. This dilution plate was then mixed and a 10 µl aliquot transferred to the final assay plate, which had been pre-filled with 40 µl/well RPMI media containing the appropriate stimulant to activate TNFα secretion (see below).

EXAMPLE 2

Assay for TNFα Suppressing Activity by the Combination of Dipyridamole and Fludrocortisone The compound dilution matrix was assayed using a TNFα ELISA method. Briefly, a 100 µl suspension of diluted human white blood cells contained within each well of a polystyrene 384-well plate (NalgeNunc) was stimulated to secrete TNFα by treatment with a final concentration of 10 ng/ml phorbol 12-myristate 13-acetate (Sigma) and 750 ng/µl ionomycin (Sigma). Various concentrations of each test compound were added at the time of stimulation. After 16-18 hours of incubation at 37° C. in a humidified incubator, the plate was centrifuged and the supernatant transferred to a white opaque polystyrene 384 well plate (NalgeNunc, Maxisorb) coated with an anti-TNF antibody (PharMingen, #18631D). After a two-hour incubation, the plate was washed (Tecan PowerWasher 384) with phosphate buffered saline (PBS) containing 0.1% Tween 20 (polyoxyethylene sorbitan monolaurate) and incubated for an additional one hour with another anti-TNF antibody that was biotin labeled (PharMingen, 18642D) and horseradish peroxidase (HRP) coupled to strepavidin (PharMingen, #13047E). After the plate was washed with 0.1% Tween 20/PBS, the HRP substrate (which contains luminol, hydrogen peroxide, and an enhancer such as para-iodophenol) was added to each well and light intensity measured using a LJL Analyst luminometer. Control wells contained a final concentration of 1 µg/ml cyclosporin A (Sigma).

Together, dipyridamole and fludrocortisone were able to suppress TNFα secretion in blood stimulated with phorbol 12-myristate 13-acetate and ionomycin. As seen in Tables 1 and 2, dipyridamole was able to enhance the potency of fludrocortisone by 60-fold. At a concentration of 947 nM, fludrocortisone alone inhibited TNFα secretion by 39%. Addition of 124 nM dipyridamole to a concentration of only 15 nM fludrocortisone resulted in the inhibition of TNFα secretion by 39% (Table 1). Efficacy was maintained while reducing the total drug species by over 80%, from 947 nM to 163 nM. In the presence of 2 µM dipyridamole, 50% TNFα inhibition is achieved by only 4 nM fludrocortisone. This level of inhibition is not possible with fludrocortisone alone at concentrations that would be expected to cause serious mineralocorticoid-induced side effects. Dipyridamole enhancement of fludrocortisone activity was observed in a secondary screen (Table 2). Again, a low dose of 495 nM dipyridamole enhanced the potency of fludrocortisone by over 135 fold. Specifically, 947 nM fludrocortisone alone was required to achieve a 52% reduction of TNFα secretion. A similar reduction (49%) was measured for the combination of 7 nM fludrocortisone and 495 nM dipyridamole. Further, the addition of 248 nM dipyridamole resulted in a supramaximal effect on the inhibition of TNFα secretion at fludrocortisone concentrations as low as 59 nM.

EXAMPLE 3

Preparation of Pairwise Compound Mixed Combination Serial Dilution Matrix

A compound matrix of dipyridamole and prednisolone were prepared according to the method of Example 1. The initial stock solution of dipyridamole was 16 mg/ml, and prednisolone was 1.6 mg/ml.

EXAMPLE 4

Assay for TNFα Suppressing Activity by the Combination of Dipyridamole and Prednisolone The compound dilution matrix of Example 3, was assayed using the TNFα ELISA method of Example 2. The results are shown in Table 3. Together, dipyridamole and prednisolone were able to suppress TNFα secretion in blood stimulated with phorbol 12-myristate 13-acetate and ionomycin to a greater extent than either compound alone. Specifically, dipyridamole greatly increased the potency of prednisolone. Prednisolone alone, at a concentration of 250 nM, can suppress TNFα secretion by 38%. The same level of suppression (41%) can be achieved by only 1 nM prednisolone in combination with 2 µM dipyridamole. This represents a shift in the potency of prednisolone of over 250-fold. Further, the addition of 2 µM dipyridamole to 250 nM prednisolone resulted in a supramaximal effect (57%), compared to prednisolone alone (38%). The combination of low doses of prednisolone and dipyridamole, therefore, results in the inhibition TNFα to levels previously unattainable without a high risk of glucocorticoid-induced side effects.

TABLE 1

Primary Screen Data of Fludrocortisone vs Dipyridamole Average Result of 2 Plates
(% TNFα suppression from P/I-induced white blood cells)

| Fludro-cortisone | Dipyridamole [µM] | | | | | |
|---|---|---|---|---|---|---|
| [µM] | 7.927 | 1.982 | 0.495 | 0.124 | 0.031 | 0.000 |
| 0.947 | 82.90 | 66.61 | 54.90 | 52.48 | 61.35 | 39.19 |
| 0.237 | 81.88 | 61.99 | 52.35 | 52.11 | 46.77 | 36.66 |
| 0.059 | 79.57 | 60.37 | 47.08 | 45.47 | 42.93 | 32.49 |
| 0.015 | 77.13 | 54.06 | 40.70 | 38.73 | 30.62 | 22.63 |
| 0.004 | 74.61 | 50.60 | 34.21 | 24.90 | 22.52 | 17.21 |
| 0.000 | 66.37 | 35.24 | 13.21 | 9.08 | 3.68 | 0.00 |

TABLE 3

Primary Screen Data of Prednisolone vs Dipyridamole Average Result of 2 Plates
(% TNFα suppression from P/I-induced white blood cells)

| Prednisolone | Dipyridamole [µM] | | | | | |
|---|---|---|---|---|---|---|
| [µM] | 7.93 | 1.98 | 0.50 | 0.12 | 0.031 | 0.00 |
| 0.250 | 70.30 | 56.72 | 48.90 | 50.82 | 46.08 | 38.25 |
| 0.063 | 68.53 | 57.68 | 51.61 | 47.24 | 37.57 | 33.00 |
| 0.016 | 66.48 | 45.20 | 40.12 | 40.99 | 32.42 | 37.84 |

TABLE 2

Secondary Screen Data of Fludrocortisone vs Dipyridamole Average Result of 2 Plates
(% TNFα Suppression from P/I-induced white blood cells)

| Fludro-cortisone | Dipyridamole [µM] | | | | | | | | |
|---|---|---|---|---|---|---|---|---|---|
| [µM] | 7.927 | 3.964 | 1.982 | 0.991 | 0.495 | 0.248 | 0.124 | 0.062 | 0.031 | 0.000 |
| 0.947 | 89.12 | 82.25 | 78.01 | 69.10 | 67.91 | 61.77 | 60.82 | 53.38 | 53.41 | 52.05 |
| 0.473 | 92.64 | 84.40 | 78.44 | 70.25 | 65.06 | 60.25 | 56.14 | 53.68 | 50.07 | 50.16 |
| 0.237 | 89.69 | 83.68 | 82.01 | 70.36 | 66.53 | 65.46 | 60.90 | 56.65 | 52.34 | 49.25 |
| 0.118 | 87.58 | 80.66 | 76.13 | 68.18 | 65.89 | 67.09 | 58.91 | 54.17 | 47.39 | 46.42 |
| 0.059 | 84.43 | 79.37 | 73.86 | 64.53 | 63.88 | 58.96 | 56.84 | 48.63 | 44.66 | 40.24 |
| 0.030 | 88.61 | 76.42 | 68.58 | 65.77 | 62.08 | 51.31 | 49.96 | 47.02 | 44.19 | 36.95 |
| 0.015 | 90.46 | 79.36 | 73.52 | 65.22 | 56.39 | 62.88 | 43.17 | 47.73 | 46.00 | 37.77 |
| 0.007 | 84.11 | 75.29 | 69.74 | 64.61 | 48.90 | 42.05 | 38.92 | 39.27 | 36.70 | 29.49 |
| 0.004 | 79.02 | 75.15 | 65.79 | 55.19 | 46.00 | 41.93 | 35.15 | 30.94 | 30.20 | 22.40 |
| 0.000 | 78.11 | 66.54 | 62.36 | 48.20 | 33.73 | 23.02 | 12.13 | 9.43 | 10.16 | -3.50 |

TABLE 3-continued

Primary Screen Data of Prednisolone vs
Dipyridamole Average Result of 2 Plates
(% TNFα suppression from P/I-induced white blood cells)

| Prednisolone [μM] | Dipyridamole [μM] | | | | | |
|---|---|---|---|---|---|---|
| | 7.93 | 1.98 | 0.50 | 0.12 | 0.031 | 0.00 |
| 0.004 | 61.06 | 47.25 | 34.66 | 33.48 | 32.42 | 19.99 |
| 0.001 | 57.35 | 40.84 | 32.10 | 25.47 | 20.64 | 4.86 |
| 0.000 | 47.51 | 27.21 | 18.30 | 12.63 | 11.24 | 0.00 |

OTHER EMBODIMENTS

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications and patent applications cited in this specification are herein incorporated by reference as if each individual publication or patent application were specifically and individually incorporated by reference.

What is claimed is:

1. A method for treating a patient who has an immunoinflammatory disorder selected from rheumatoid arthritis, psoriasis, ulcerative colitis, Crohn's disease, ankylosing spondylitis, or multiple sclerosis, said method comprising administering to said patient:
   (a) a corticosteroid; and
   (b) dipyridamole, wherein said dipyridamole and said corticosteroid are administered simultaneously or within one hour of each other, in amounts and for a duration sufficient to treat said patient, and wherein said dipyridamole is administered orally or intravenously.

2. The method of claim 1, wherein said corticosteroid is algestone, 6-alpha-fluoroprednisolone, 6-alpha-methylprednisolone, 6-alpha-methylprednisolone 21-acetate, 6-alpha-methylprednisolone 21-hemisuccinate sodium salt, 6-alpha,9-alpha-difluoroprednisolone 21-acetate 17-butyrate, ameinafal, beclomethasone, beclomethasone dipropionate, beclomethasone dipropionate monohydrate, 6-beta-hydroxycortisol, betamethasone, betamethasone-17-valerate, budesonide, clobetasol, clobetasol propionate, clobetasone, clocortolone, clocortolone pivalate, cortisone, cortisone acetate, cortodoxone, deflazacort, 21-deoxycortisol, deprodone, descinolone, desonide, desoximethasone, dexamethasone, dexamethasone-21-acetate, dichlorisone, diflorasone, diflorasone diacetate, diflucortolone, doxibetasol, fludrocortisone, flumethasone, flumethasone pivalate, flumoxonide, flunisolide, fluocinonide, fluocinolone acetonide, 9-fluorocortisone, fluorohydroxyandrostenedione, fluorometholone, fluorometholone acetate, fluoxymesterone, flupredidene, fluprednisolone, flurandrenolide, formocortal, halcinonide, halometasone, halopredone, hyrcanoside, hydrocortisone, hydrocortisone acetate, hydrocortisone butyrate, hydrocortisone cypionate, hydrocortisone sodium phosphate, hydrocortisone sodium succinate, hydrocortisone probutate, hydrocortisone valerate, 6-hydroxydexamethasone, isoflupredone, isoflupredone acetate, isoprednidene, meclorisone, methyiprednisolone, methyiprednisolone acetate, methyiprednisolone sodium succinate, paramethasone, paramethasone acetate, prednisolone, prednisolone acetate, prednisolone metasulphobenzoate, prednisolone sodium phosphate, prednisolone tebutate, prednisolone-21-hemisuccinate free acid, prednisolone-21-acetate, prednisolone-21(beta-D-glucuronide), prednisone, prednylidene, procinonide, tralonide, triamcinolone, triamcinolone acetonide, triamcinolone acetonide 21-palmitate, triamcinolone diacetate, triamcinolone hexacetonide, or wortmannin.

3. The method of claim 2, wherein said corticosteroid is prednisone or prednisolone.

4. The method of claim 1, wherein said dipyridamole and said corticosteroid are administered simultaneously.

5. The method of claim 4, wherein said dipyridamole and said corticosteroid are administered in the same pharmaceutical formulation.

6. The method of claim 1, wherein said immunoinflammatory disorder is rheumatoid arthritis, psoriasis, ulcerative colitis, or Crohn's disease.

7. The method of claim 6, wherein said immunoinflammatory disorder is rheumatoid arthritis.

8. The method of claim 6, wherein said immunoinflammatory disorder is psoriasis.

9. The method of claim 1, wherein said dipyridamole is administered in an amount of 5 to 600 mg/day, and said corticosteroid is administered in an amount of 0.1-1500 mg/day.

10. The method of claim 9, wherein said dipyridamole is administered in an amount of 50 to 400 mg/day, and said corticosteroid is administered in an amount of 0.5-30 mg/day.

11. The method of claim 10, wherein said corticosteroid is administered in an amount of 0.5-10 mg/day.

12. A method for treating a patient who has an immunoinflammatory disorder selected from rheumatoid arthritis, psoriasis, ulcerative colitis, Crohn's disease, ankylosing spondylitis, or multiple sclerosis, said method comprising orally or intravenously administering to said patient a composition comprising dipyridamole and a corticosteroid in an amount and for a duration sufficient to treat said patient.

13. The method of claim 12, wherein said corticosteroid is algestone, 6-alpha-fluoroprednisolone, 6-alpha-methylprednisolone, 6-alpha-methylprednisolone 21-acetate, 6-alpha-methylprednisolone 21-hemisuccinate sodium salt, 6-alpha,9-alpha-difluoroprednisolone 21-acetate 17-butyrate, amcinafal, beclomethasone, beclomethasone dipropionate, beclomethasone dipropionate monohydrate, 6-beta-hydroxycortisol, betamethasone, betamethasone-17-valerate, budesonide, clobetasol, clobetasol propionate, clobetasone, clocortolone, clocortolone pivalate, cortisone, cortisone acetate, cortodoxone, deflazacort, 21-deoxycortisol, deprodone, descinolone, desonide, desoximethasone, dexamethasone, dexamethasone-21-acetate, dichlorisone, diflorasone, diflorasone diacetate, diflucortolone, doxibetasol, fludrocortisone, flumethasone, flumethasone pivalate, flumoxonide, flunisolide, fluocinonide, fluocinolone acetonide, 9-fluorocortisone, fluorohydroxyandrostenedione, fluorometholone, fluorometholone acetate, fluoxymesterone, flupredidene, fluprednisolone, flurandrenolide, formocortal, halcinonide, halometasone, halopredone, hyrcanoside, hydrocortisone, hydrocortisone acetate, hydrocortisone butyrate, hydrocortisone cypionate, hydrocortisone sodium phosphate, hydrocortisone sodium succinate, hydrocortisone probutate, hydrocortisone valerate, 6-hydroxydexamethasone, isoflupredone, isoflupredone acetate, isoprednidene, meclorisone, methyiprednisolone, methyiprednisolone acetate, methyiprednisolone sodium succinate, paramethasone, paramethasone acetate, prednisolone, prednisolone acetate, prednisolone metasulphobenzoate, prednisolone sodium phosphate, prednisolone tebutate, prednisolone-21-hemisuccinate free acid, prednisolone-21-acetate, prednisolone-21(beta-D-glucuronide), prednisone, prednylidene, procinonide, tralonide, triamcinolone, triamcinolone acetonide, triamcinolone acetonide 21-palmitate, triamcinolone diacetate, triamcinolone hexacetonide, or wortmannin.

14. The method of claim 13, wherein said corticosteroid is prednisone or prednisolone.

15. The method of claim 14, wherein said composition comprises 0.5 to 10 mg of prednisone or prednisolone.

16. The method of claim 12, wherein said immunoinflammatory disorder is rheumatoid arthritis, psoriasis, ulcerative colitis, or Crohn's disease.

17. The method of claim 16, wherein said composition is administered intravenously.

18. The method of claim 17, wherein said corticosteroid is prednisone or prednisolone.

19. The method of claim 16, wherein said composition is administered orally.

20. The method of claim 16, wherein said corticosteroid is prednisone or prednisolone.

21. The method of claim 19, wherein said corticosteroid is prednisone or prednisolone.

22. The method of claim 12, wherein said composition is administered intravenously.

23. The method of claim 12, wherein said composition is administered orally.

24. The method of claim 12, wherein said composition comprises 5 to 600 mg of dipyridamole.

25. The method of claim 24, wherein said composition comprises 50 to 400 mg of dipyridamole.

26. A method for treating a patient who has rheumatoid arthritis, said method comprising orally administering to said patient a composition comprising dipyridamole and a corticosteroid in an amount and for a duration sufficient to treat said patient.

27. The method of claim 26, wherein said composition consists of active ingredients and excipients, wherein said active ingredients consist of a corticosteroid and dipyridamole.

28. The method of claim 26, wherein said composition comprises 5 to 600 mg of dipyridamole.

29. The method of claim 28, wherein said composition comprises 50 to 400 mg of dipyridamole.

30. The method of claim 26, wherein said corticosteroid is prednisone or prednisolone.

31. The method of claim 30, wherein said composition comprises 0.5 to 10 mg of prednisone or prednisolone.

32. A method for treating a patient who has psoriasis, said method comprising orally administering to said patient a composition comprising dipyridamole and a corticosteroid in an amount and for a duration sufficient to treat said patient.

33. The method of claim 32, wherein said composition consists of active ingredients and excipients, wherein said active ingredients consist of a corticosteroid and dipyridamole.

34. The method of claim 32, wherein said composition comprises 5 to 600 mg of dipyridamole.

35. The method of claim 34, wherein said composition comprises 50 to 400 mg of dipyridamole.

36. The method of claim 32, wherein said corticosteroid is prednisone or prednisolone.

37. The method of claim 36, wherein said composition comprises 0.5 to 10 mg of prednisone or prednisolone.

38. A method for treating a patient who has ulcerative colitis, said method comprising orally administering to said patient a composition comprising dipyridamole and a corticosteroid in an amount and for a duration sufficient to treat said patient.

39. The method of claim 38, wherein said composition consists of active ingredients and excipients, wherein said active ingredients consist of a corticosteroid and dipyridamole.

40. The method of claim 38, wherein said composition comprises 5 to 600 mg of dipyridamole.

41. The method of claim 40, wherein said composition comprises 50 to 400 mg of dipyridamole.

42. The method of claim 38, wherein said corticosteroid is prednisone or prednisolone.

43. The method of claim 42, wherein said composition comprises 0.5 to 10 mg of prednisone or prednisolone.

44. A method for treating a patient who has Crohn's disease, said method comprising orally administering to said patient a composition comprising dipyridamole and a corticosteroid in an amount and for a duration sufficient to treat said patient.

45. The method of claim 44, wherein said composition consists of active ingredients and excipients, wherein said active ingredients consist of a corticosteroid and dipyridamole.

46. The method of claim 44, wherein said composition comprises 5 to 600 mg of dipyridamole.

47. The method of claim 46, wherein said composition comprises 50 to 400 mg of dipyridamole.

48. The method of claim 44, wherein said corticosteroid is prednisone or prednisolone.

49. The method of claim 48, wherein said composition comprises 0.5 to 10 mg of prednisone or prednisolone.

50. A method for treating a patient who has an immunoinflammatory disorder selected from rheumatoid arthritis, psoriasis, ulcerative colitis, Crohn's disease, ankylosing spondylitis, or multiple sclerosis, said method comprising orally or intravenously administering to said patient a composition consisting of active ingredients and excipients, wherein said active ingredients consist of a corticosteroid and dipyridamole, in an amount and for a duration sufficient to treat said patient.

51. The method of claim 50, wherein said composition comprises 5 to 600 mg of dipyridamole.

52. The method of claim 51, wherein said composition comprises 50 to 400 mg of dipyridamole.

53. The method of claim 50, wherein said corticosteroid is prednisone or prednisolone.

54. The method of claim 53, wherein said composition comprises 0.5 to 10 mg of prednisone or prednisolone.

* * * * *

UNITED STATES PATENT AND TRADEMARK OFFICE
CERTIFICATE OF CORRECTION

PATENT NO. : 7,253,155 B2
APPLICATION NO. : 10/264991
DATED : August 7, 2007
INVENTOR(S) : Keith et al.

It is certified that error appears in the above-identified patent and that said Letters Patent is hereby corrected as shown below:

Under item 56
Page 2, Column 2, On the Title Page, in OTHER PUBLICATIONS, in
   Barlow et al., replace "pyrimidines that" with --pyrimidines that--.

Page 2, Column 2, On the Title Page, in OTHER PUBLICATIONS, in
   Brunette et al., replace "Pediatr. Nephrol." with --*Pediatr. Nephrol.*--.

Page 2, Column 2, On the Title Page, in OTHER PUBLICATIONS, in
   Bruserud, replace "Clin. Immunol. Immunopathol." with --*Clin. Immunol. Immunopathol.*--.

Page 2, Column 2, On the Title Page, in OTHER PUBLICATIONS, in
   Eigler et al., replace "Scan J. Immunol." with --*Scan. J. Immunol.*--.

Page 2, Column 2, On the Title Page, in OTHER PUBLICATIONS, in
   Hasko et al., replace "FASEB J." with --*FASEB J.*--.

Page 2, Column 2, On the Title Page, in OTHER PUBLICATIONS, in
   Iijima et al., replace "Pediatr. Nephrol." with --*Pediatr. Nephrol.*--.

Page 2, Column 2, On the Title Page, in OTHER PUBLICATIONS, in
   Nenci et al., replace "Respiration" with --*Respiration*--.

Page 2, Column 2, On the Title Page, in OTHER PUBLICATIONS, in
   Rossi et al., replace "JAMA" with --*JAMA*--.

Page 2, Column 2, On the Title Page, in OTHER PUBLICATIONS, in
   Wagner et al., replace "Circ. Res." with --*Circ. Res.*--.

Page 2, Column 2, On the Title Page, in OTHER PUBLICATIONS, in
   Yoshikawa et al., replace "Nephrol Dial Transplant" with --*Nephrol. Dial. Transplant*--.

UNITED STATES PATENT AND TRADEMARK OFFICE
CERTIFICATE OF CORRECTION

PATENT NO. : 7,253,155 B2
APPLICATION NO. : 10/264991
DATED : August 7, 2007
INVENTOR(S) : Keith et al.

It is certified that error appears in the above-identified patent and that said Letters Patent is hereby corrected as shown below:

Page 2, Column 2, On the Title Page, in OTHER PUBLICATIONS, in Berger et al., replace "Berger et al., "Comparative Carcinogenic Activity of" with --Berger et al., "Comparative Carcinogenic Activity of--

Page 2, Column 2, On the Title Page, in OTHER PUBLICATIONS, in Berger et al., replace "Prednisolone in Sprague-Dawley Rats," *Arch. Geschwulstforsch55:*" with --Prednisolone in Sprague-Dawley Rats," *Arch. Geschwulstforsch* 55:--

Column 6, Line 4, replace "6-alpha, 9-alpha-difluoroprednisolone" with --6-alpha, 9-alpha-difluoroprednisolone--.

Column 6, Line 51, replace "the vivo" with --*the in vivo*--.

Column 7, Line 47, replace "recovery" with --recover--.

Column 11, Line 29, replace "poly-(isobutyl cyanoacrylate), poly(2-hydroxyethyl-L-glutamnine)" with --poly-(isobutyl cyanoacrylate), poly(2-hydroxyethyl-L-glutamine)--.

Column 18, Line 48, replace "6-alpha,9-alpha-difluoroprednisolone" with --6-alpha, 9-alpha-difluoroprednisolone--.

Signed and Sealed this

Seventeenth Day of June, 2008

JON W. DUDAS
*Director of the United States Patent and Trademark Office*